United States Patent
Gunaratne et al.

(10) Patent No.: US 9,824,286 B2
(45) Date of Patent: *Nov. 21, 2017

(54) METHOD AND APPARATUS FOR EARLY DETECTION OF DYNAMIC ATTENTIVE STATES FOR PROVIDING AN INATTENTIVE WARNING

(71) Applicants: TOYOTA JIDOSHA KABUSHIKI KAISHA, Toyota-shi (JP); CENTRAL MICHIGAN UNIVERSITY, Mount Pleasant, MI (US)

(72) Inventors: Pujitha Gunaratne, Windsor (CA); Richard W. Backs, Mount Pleasant, MI (US)

(73) Assignees: TOYOTA JIDOSHA KABUSHIKI KAISHA, Toyota-shi (JP); CENTRAL MICHIGAN UNIVERSITY, Mount Pleasant, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/052,211

(22) Filed: Feb. 24, 2016

(65) Prior Publication Data

US 2016/0171322 A1 Jun. 16, 2016

Related U.S. Application Data

(63) Continuation of application No. 14/447,752, filed on Jul. 31, 2014, now Pat. No. 9,299,237, which is a (Continued)

(51) Int. Cl.
*G08B 23/00* (2006.01)
*G06K 9/00* (2006.01)
(Continued)

(52) U.S. Cl.
CPC ........ *G06K 9/00845* (2013.01); *A61B 5/1128* (2013.01); *A61B 5/18* (2013.01);
(Continued)

(58) Field of Classification Search
CPC ............... G08G 1/163; G06K 9/00832; G06K 9/00771; G06K 9/00604; B60K 35/00; A61B 5/18; A61B 5/7221
(Continued)

(56) References Cited

U.S. PATENT DOCUMENTS 7,403,124 B2 * 7/2008 Arakawa ............... B60K 28/066
340/576
7,633,383 B2 * 12/2009 Dunsmoir .......... G06K 9/00805
340/435

(Continued)

FOREIGN PATENT DOCUMENTS

JP 2009-018625 A2 1/2009

*Primary Examiner* — Hoi Lau
(74) *Attorney, Agent, or Firm* — Oblon, McClelland, Maier & Neustadt, L.L.P.

(57) ABSTRACT

A method and apparatus for determining an inattentive state of an operator of a vehicle and for providing information to the operator of the vehicle by obtaining face images of the operator of the vehicle, obtaining images of an environment of the vehicle, determining one or more areas of interest in the environment of the vehicle based on the images of the environment, obtaining, from a relevance and priority database, relevance and priority values corresponding to the one or more areas of interest, determining a probability of attention of the operator of the vehicle to the one or more areas of interest based on the images of the environment and the relevance and priority values, determining an attention deficiency based on the determined probability of attention
(Continued)

and the face images, and providing the information to the operator of the vehicle based on the determined attention deficiency.

20 Claims, 5 Drawing Sheets

Related U.S. Application Data continuation of application No. 13/750,137, filed on Jan. 25, 2013, now Pat. No. 8,847,771.

(51) Int. Cl.
*A61B 5/18* (2006.01)
*B60K 28/06* (2006.01)
*G08B 21/04* (2006.01)
*A61B 5/00* (2006.01)
*A61B 3/113* (2006.01)
*A61B 5/11* (2006.01)
*G08G 1/16* (2006.01)

(52) U.S. Cl.
CPC ........ *B60K 28/066* (2013.01); *G06K 9/00604* (2013.01); *G08B 21/0476* (2013.01); *A61B 3/113* (2013.01); *A61B 5/1103* (2013.01); *A61B 5/6893* (2013.01); *G08G 1/165* (2013.01); *G08G 1/166* (2013.01); *Y02T 10/84* (2013.01)

(58) Field of Classification Search
USPC ........ 340/576, 575, 438; 345/633, 168, 156, 345/158; 348/77, 144, 78, 240.99, 739, 348/345, 23.99, 222.1, 349
See application file for complete search history.

(56) References Cited

U.S. PATENT DOCUMENTS

| | | | | |
|---|---|---|---|---|
| 7,884,705 B2* | 2/2011 | Nishimura | ............ | G08G 1/166 180/272 |
| 8,085,140 B2* | 12/2011 | Mochizuki | ............ | B60W 40/02 340/435 |
| 2004/0090334 A1* | 5/2004 | Zhang | .................... | G08B 21/06 340/575 |
| 2004/0239509 A1* | 12/2004 | Kisacanin | ................ | A61B 5/18 340/575 |
| 2006/0103539 A1* | 5/2006 | Isaji | .......................... | B60J 3/04 340/575 |
| 2007/0159344 A1* | 7/2007 | Kisacanin | .......... | G06K 9/00362 340/576 |
| 2008/0084499 A1* | 4/2008 | Kisacanin | .............. | A61B 3/113 348/370 |
| 2009/0268022 A1* | 10/2009 | Omi | ....................... | G08B 21/06 348/135 |
| 2009/0273687 A1* | 11/2009 | Tsukizawa | .............. | G06F 3/012 348/222.1 |
| 2010/0033333 A1* | 2/2010 | Victor | .................... | A61B 3/113 340/576 |
| 2010/0049375 A1* | 2/2010 | Tanimoto | .................. | B60T 7/12 701/1 |
| 2010/0129263 A1* | 5/2010 | Arakawa | ................ | A61M 21/00 422/105 |
| 2010/0202658 A1* | 8/2010 | Ishida | ...................... | A61B 5/18 382/103 |
| 2010/0241021 A1* | 9/2010 | Morikawa | .............. | A61B 5/048 600/544 |
| 2010/0265074 A1* | 10/2010 | Namba | .............. | G06K 9/00771 340/576 |
| 2011/0169625 A1* | 7/2011 | James | .................... | B60Q 9/008 340/439 |
| 2012/0002027 A1* | 1/2012 | Takahashi | ............ | B60K 28/066 348/77 |
| 2012/0050138 A1* | 3/2012 | Sato | ....................... | B60K 35/00 345/4 |
| 2012/0154441 A1* | 6/2012 | Kim | .................... | G06K 9/00832 345/633 |
| 2013/0057671 A1* | 3/2013 | Levin | ................... | A61B 5/7221 348/78 |
| 2013/0073115 A1* | 3/2013 | Levin | ...................... | A61B 5/18 701/1 |
| 2013/0162794 A1* | 6/2013 | Wakiyama | ................ | A61B 5/18 348/77 |
| 2014/0062704 A1* | 3/2014 | Kubotani | ................ | G08B 21/06 340/575 |
| 2014/0125474 A1* | 5/2014 | Gunaratne | ............. | G08G 1/163 340/439 |
| 2014/0139655 A1* | 5/2014 | Mimar | .............. | G08B 21/0476 348/77 |

* cited by examiner

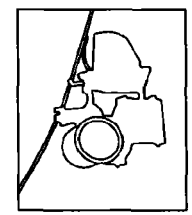
Priority light
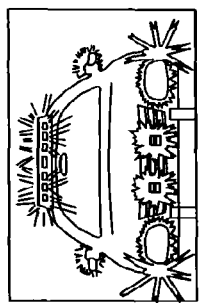
Priority/emergency vehicle light
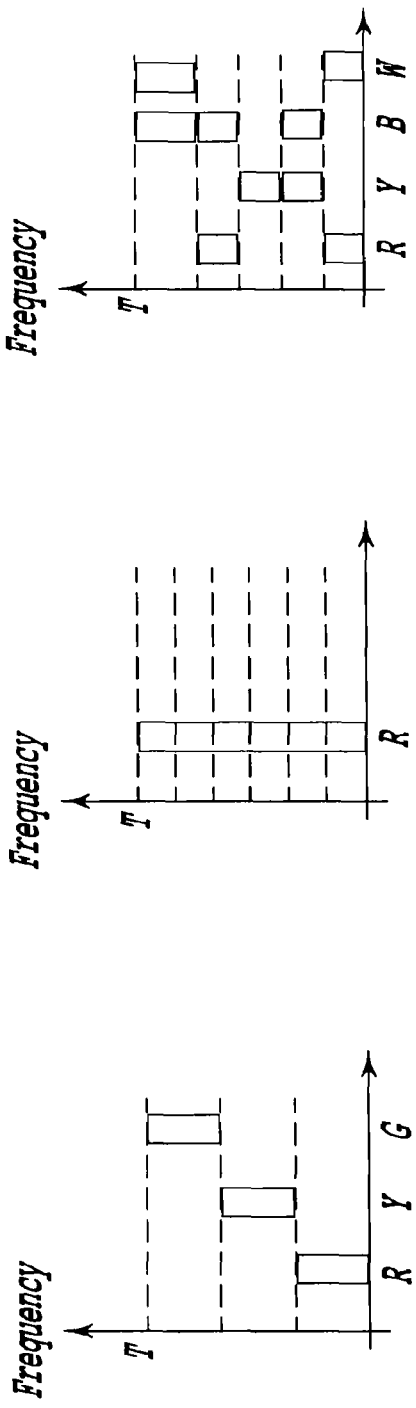
FIG. 5A
FIG. 5B
FIG. 5C

METHOD AND APPARATUS FOR EARLY DETECTION OF DYNAMIC ATTENTIVE STATES FOR PROVIDING AN INATTENTIVE WARNING

CROSS-REFERENCE TO RELATED APPLICATIONS

This application is a continuation of and claims the benefit of priority under 35 U.S.C. §120 from U.S. application Ser. No. 14/447,752, filed Jul. 31, 2014 which is a continuation of U.S. application Ser. No. 13/750,137 (now U.S. Pat. No. 8,847,771), filed Jan. 25, 2013, the entire contents of which are incorporated herein by reference.

FIELD

The present disclosure generally relates to a method and apparatus for early detection of dynamic attentive states and for providing an inattentive warning. More specifically, the present disclosure relates to a method and apparatus for early detection of dynamic attentive states based on an operator's eye movements and surround features for providing inattentive warning.

BACKGROUND

Conventionally, attention allocation models based on saliency, effort, expectancy, and value, have been used in selective attention research, and have been applied mainly in aviation. Attention allocation of airplane pilots during flight related tasks such as aviating, navigating, and landing, is conventionally experimented with secondary tasks of monitoring in-flight traffic displays and communicating with air traffic control centers.

Moreover, a variation of this approach has been tested in surface driving situations to analyze required attention levels for proper maneuvers while engaged in secondary in-vehicular tasks. Such conventional approaches describe selective attention models to predict the attention of an operator to static areas of interest (AOIs) in operation of the vehicle and secondary in-vehicle tasks.

SUMMARY

The inventors discovered that these conventional approaches do not provide accurate predictions of the operator perception for complex environment events. Also, these conventional approaches are not capable of predicting how the operator would react to the occurrence of an unperceived event.

The present disclosure provides a method and apparatus for early detection of dynamic attentive state based on an operator's eye movements and surround features for providing an inattentive warning.

According to an embodiment of the present disclosure, there is provided a method and apparatus for determining an inattentive state of an operator of a vehicle and for providing information to the operator of the vehicle by obtaining, via a first camera, facial images of the operator of the vehicle, obtaining, via a second camera, images of an environment of the vehicle, determining one or more areas of interest in the environment of the vehicle based on the images of the environment of the vehicle, obtaining, from a relevance and priority database, relevance and priority values corresponding to the one or more areas of interest, determining a probability of attention of the operator of the vehicle to the one or more areas of interest based on the images of the environment of the vehicle and the relevance and priority values, determining an attention deficiency based on the determined probability of attention and the facial images, and providing, via a warning/guidance device, the information to the operator of the vehicle based on the determined attention deficiency.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the embodiments described herein, and many of the attendant advantages thereof will be readily obtained as the same becomes better understood by reference to the following detailed description when considered in connection with the accompanying drawings, wherein:

FIGS. 5A-5C illustrate examples of bandwidth estimation based on frequency analysis applied to various traffic light scenarios.

DETAILED DESCRIPTION

According to one embodiment, there is provided a method and apparatus to predict the allocation of attention to multiple dynamic AOIs in the environment of an operator, thus providing an attention estimate for the external events.

According to one embodiment, a method and apparatus is provided to predict how the operator would react to the occurrence of an unexpected event in the environment once perceived without prior attention.

The present disclosure also describes the countermeasures for possible erratic actions as a result of such unexpected events.

According to one embodiment, a method is described to estimate the attention on multiple dynamic AOIs in the environment of the vehicle operation, learn normal/ideal operator scanning behavior for different AOIs, and predict inattentiveness by thresholding learned values against observed values.

According to one embodiment, a method is described to learn operator's reaction patterns to unexpected events and issue variable active warnings based on the predictions.

According to one embodiment, there is provided a method and apparatus that is capable of warning an operator in fail-to-look and look-but-fail-to-see situations.

Figure 1:
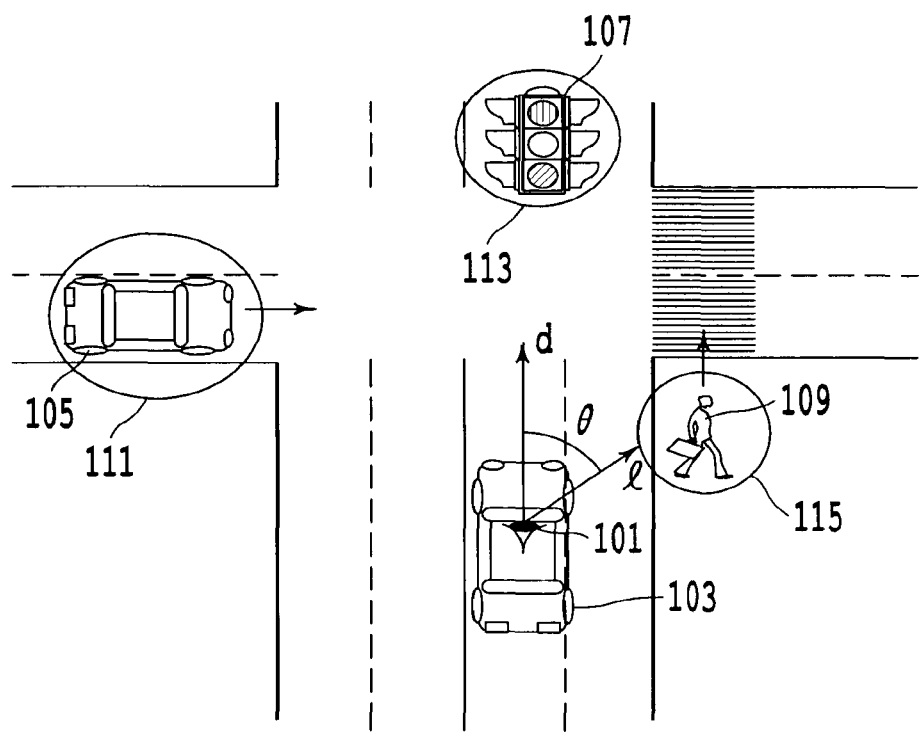
FIG. 1 illustrates an example environment seen by the eyes of an operator of a vehicle.

Referring now to the drawings, wherein like reference numerals designate identical or corresponding parts throughout the several views, FIG. 1 illustrates an example environment as seen from the perspective 101 of an operator of a vehicle 103. In this example, the environment includes another vehicle 105, a traffic light 107, and a pedestrian 109. As shown in FIG. 1, an AOI is defined for each object in the environment of the vehicle 103. AOI-1 111 corresponds to the other vehicle 105, AOI-2 113 corresponds to the traffic light 107, and AOI-3 115 corresponds to the pedestrian 109.

Figure 2:
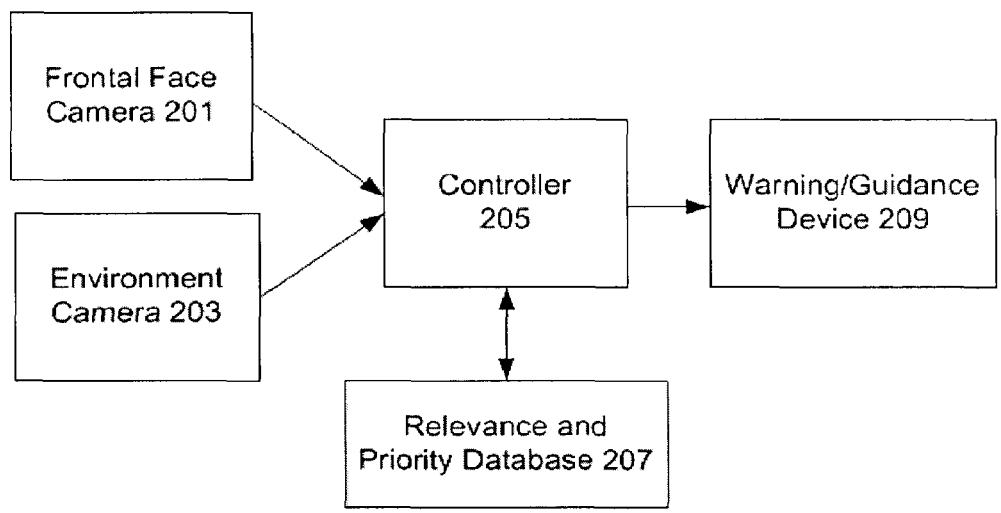
FIG. 2 shows a block diagram of a system for early detection of dynamic attentive state of an operator of a vehicle, and for providing warnings and guidance according to one embodiment.

FIG. 2 is a block diagram of a system for early detection of a dynamic attentive state of an operator of a vehicle, and for providing warnings and guidance according to one embodiment. As shown in FIG. 2, a controller 205 obtains face images from face camera 201, and environment images from environment camera 203, and activates a warning/guidance device 209 based on the information from the face camera 201 and the environment camera 203 and a relevance and priority database 207. Details of the method performed by the controller 205 will be described with reference to FIG. 3.

Figure 3:
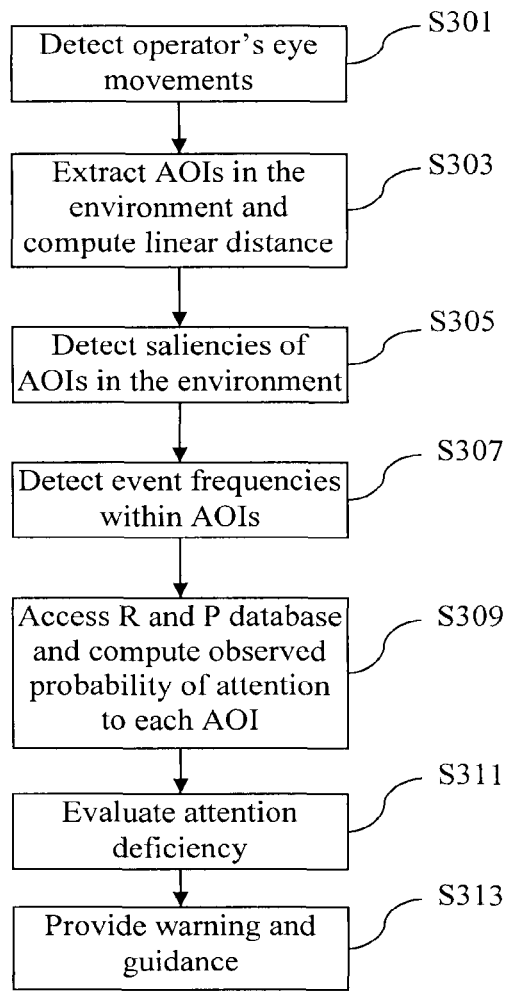
FIG. 3 is a flowchart of a method for early detection of a dynamic attentive state of an operator of a vehicle, and for providing warnings and guidance according to one embodiment.

FIG. 3 is a flowchart of a method for early detection of dynamic attentive state of an operator of a vehicle, and for providing warnings and guidance according to one embodiment.

In step S301, the operator's eye movements are detected and the operator's eye movement parameter values are determined based on the face images. The operator's eye movement parameter values may include operator gaze pointers to the scene, and the dwell time on different areas of the scene. To compute gaze pointer and dwell time, features in the eye region such as iris and pupil location are used. The gaze vector can be generated using parameters such as the location of the iris and the angle to the iris calculated with respect to the optical axis. The gaze vector can then be produced by extending a line from the iris using a computed angle from the optical axis to the outside scene as observed by the forward roadway camera. Thus, the dwell time can be a derivation of rate of change of angle to the optical axis.

The operator's face images are recorded using a camera. The camera may be mounted on the dashboard or may be included in the rear view mirror assembly or any other location inside the vehicle such that the camera can capture the face images of the driver.

According to one embodiment, the operator's eye movements are detected by detecting facial features, such as, eye corners, upper and lower eyelid features, etc. from the face image. Feature point extraction algorithms may be used to extract those features, such as, eye corners and upper and lower eyelid features. Iris and pupil locations are then detected and extracted based on the detected eye corners and upper and lower eyelid features. The iris and (/or) pupil location coordinates are then mapped with external forward images to determine the gaze pointers on external environment. Finally, gaze fixation dwell times are computed for different regions that represent AOIs in the scene.

In step S303, features are extracted in the environment recorded by cameras mounted on the vehicle, facing the forward or backward roadway and/or the periphery. These features are then used to define and segment AOIs in the scene, e.g., traffic lights, traffic signs, other vehicles on the road, pedestrians, cyclists, or animals. The linear distance from each AOI to the vehicle is also computed. For example, for AOI-3 115 shown in FIG. 1, the linear distance l can be computed as $$l = \frac{d}{\cos\theta},$$

where d is the longitudinal displacement and θ is the angle between a forward line-of-sight and the line-of-sight corresponding to AOI-3, as shown in FIG. 1. The linear distance l is used to compute the visual displacement parameter γ, where $$\gamma = \begin{cases} l & \text{if } (0 \le \theta < 90) \\ 0 & \text{otherwise} \end{cases}.$$

γ is later used in step S309 to compute the probability of attention to a given AOI.

In step S305, saliencies in each AOI are extracted and a saliency map of the environment is built from the images obtained with cameras facing the forward or backward roadway and/or the periphery. Image analysis algorithms may be applied to detect motion, color intensity, and/or texture of different objects to determine the saliency levels of that object. Steps S301, S303, and S305 can be independent and performed simultaneously by the controller.

In step S307, micro analysis of saliency variations is performed to detect events that occur within the AOI boundary and the frequency of the detected events are recorded. According to one embodiment, pattern analysis algorithms are applied for each identified AOI to detect the events that occur within the AOI boundary. These events are segmented and their frequency of occurrence is computed.

As an example, frequency analysis of a traffic signal light is performed by using the detection results of step S303 to detect a traffic light box. Further segmentations are done to separate individual light positions. Blinking, solid state, or changing frequencies of these lights are then recorded.

In step S309, relevance and priority values stored in a database, and the saliency, frequency, and linear distance values computed in steps S303, S305, and S307 are used to compute a probability of attention to each AOI in the scene. According to one embodiment, a probability of attention to AOI$_i$ is determined by:

$$P(AOI_i) = \sum_{t=t_0}^{t'} [S_{i,t} + (B_{i,t})(R_{i,t})(P_{i,t})](\gamma_{i,t}), \quad (1)$$

where B, R, and P parameters indicate the bandwidth, relevance, and priority values for AOI$_i$, and $\gamma_{i,t}$ is the displacement parameter for AOI$_i$ at time t. Bandwidth is computed based on the frequency of events computed in step S307.

The bandwidth can be computed as a summation of frequency of occurrence of events in a given AOI. Thus, for a given sampling time T, the bandwidth B can be given as, $$B = \sum_{t=t_0}^{T} \sum_{i=1}^{n} f_{E_{i,t}}$$

Where, t0 is the start of the sampling time and n denotes the number of events (E) in the AOI. For example, in a normal operation of a traffic light, alternate occurrences of each light event will be observed within the sampling time T. However, in a priority situation, one light event, most likely Red or Yellow will blink frequently. In such a case, a higher bandwidth corresponds to a higher frequency of blinks observed than the frequency in a normal operation of a traffic light. In a situation of an emergency or high priority vehicle, such as a patrol car or an ambulance, multiple events corresponding to multiple lights may blink simultaneously, producing higher bandwidth than other previous situations described. See FIG. 5.

Relevance and priority values can be obtained from pre-computed datasets and stored in a database. Saliency values are from step S305, and the visual displacement parameter $\gamma_{i,t}$ is from step S303.

The database values of R and P may be pre-estimated for different traffic situations and different objects that correspond to real world AOIs. This may be done by, e.g., a survey of experienced operators who evaluate relevance and priority values for different objects in the scene and different traffic conditions. For example, in a given intersection scenario, expert operators evaluate relevance and priority values of real world AOIs such as other vehicles, different types of traffic lights, traffic signs, pedestrians, or animals. Median and standard deviation values for these objects are then computed and stored in the database.

In step S311, attention deficiency level is computed based on a currently observed attention level and an ideally expected attention level. An operator's reaction to unexpected events is also predicted based on the degree of attention deficiency. According to one embodiment, attention deficiency level $\phi$ is:

$$\phi = P(AOI_{t,i}^{ob}) - P(AOI_{t,i}^{id}) \qquad (2),$$

where $P(AOI_{t,i}^{ob})$ is the observed attention level to $AOI_i$ at time t, and $P(AOI_{t,i}^{id})$ is the ideal attention level to $AOI_i$ at time t derived for a similar traffic situation. The attention level to a given AOI has a positive correlation with eye gaze dwell time on that AOI. Therefore, according to one embodiment, the observed level of attention $P(AOI_{t,i}^{ob})$ to $AOI_i$ at time t is the average eye gaze dwell time computed for $AOI_i$ at time t.

The ideal attention value for the $AOI_i$ at time t, $P(AOI_{t,i}^{id})$, is $$I(AOI_i) = \sum_{t=t_0}^{t_1} [S_{i,t} + (B_{i,t})(R_{i,t})(P_{i,t})](\gamma_{i,t}). \qquad (3)$$

The attention level measurement time window is chosen to be greater than the sampling frequency of the parameters. For example, when the attention level is measured at 3 sec epochs, saliency $S_{i,t}$, bandwidth $B_{i,t}$, relevance $R_{i,t}$, priority $P_{i,t}$, and visual displacement $\gamma_{i,t}$ parameters may be sampled at 100 ms, and $$I(AOI_i) = \sum_{t=t_0}^{t_0+3} [S_{i,t} + (B_{i,t})(R_{i,t})(P_{i,t})](\gamma_{i,t}).$$

In order to evaluate attention deficiency, $\phi$ is thresholded against a threshold value $\xi$ $$\phi < \xi$$

where $\xi$ corresponds to a lower bound of attention. The threshold value $\xi$ may be empirically determined for a control set of operators with different experiences to determine, e.g., the look-but-fail-to-see situation. In fail-to-look situations, gaze dwell time is zero and $\xi$ may be set as a negative value.

In step S313, based on the environment severity level, an appropriate warning and guidance is issued to the operator. For example, when $\xi$ is a negative value indicating the operator's failure to look at a critical AOI in the scene, audio-visual warnings or, based on the crash criticality, pre-crash safety procedures may be deployed. As another example, when $\phi < \xi$, guidance mechanisms such as visual indications of highlighted AOIs on, e.g., heads up display units may be issued.

Next, a hardware description of the controller 205 according to exemplary embodiments is described with reference to FIG. 4. The controller 205 may be used to perform any of the processes described in the present disclosure.

Figure 4:
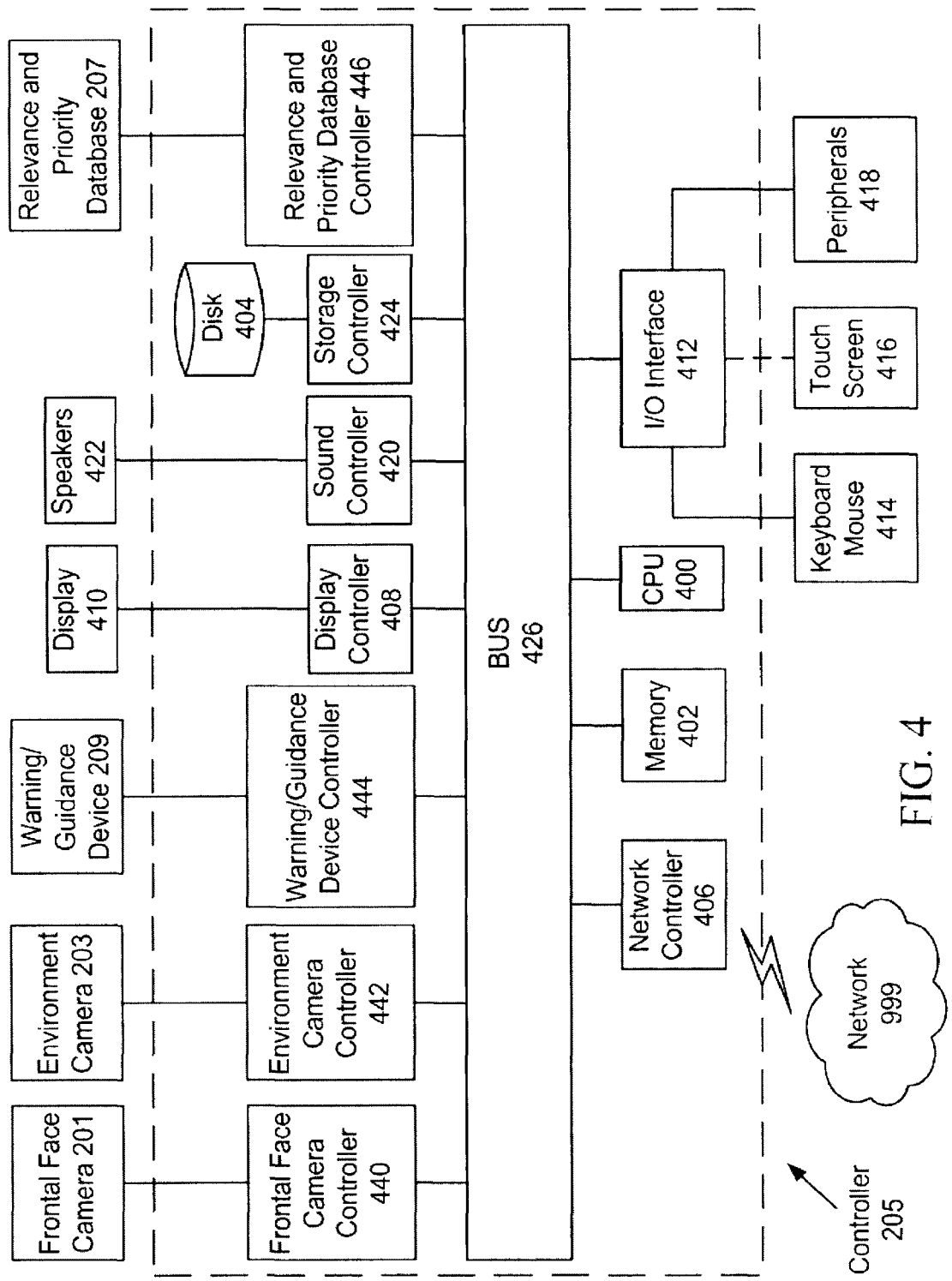
FIG. 4 is a block diagram of a controller for implementing the early detection of a dynamic attentive state of an operator.

In FIG. 4, the controller 205 includes a CPU 400 which performs the processes described above. The process data and instructions may be stored in memory 402. These processes and instructions may also be stored on a storage medium disk 404 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the controller 205 communicates, such as a server or computer.

Further, the claimed advancements may be provided as a utility application, background daemon, or component of an operating system, or combination thereof, executing in conjunction with CPU 400 and an operating system such as Microsoft Windows 7, UNIX, Solaris, LINUX, Apple MAC-OS and other systems known to those skilled in the art.

CPU 400 may be a Xenon or Core processor from Intel of America or an Opteron processor from AMD of America, or may be other processor types that would be recognized by one of ordinary skill in the art. Alternatively, CPU 400 may be implemented on an FPGA, ASIC, PLD or using discrete logic circuits, as one of ordinary skill in the art would recognize. Further, CPU 400 may be implemented as multiple processors cooperatively working in parallel to perform the instructions of the inventive processes described above.

The controller 205 in FIG. 4 also includes a network controller 406, such as an Intel Ethernet PRO network interface card from Intel Corporation of America, for interfacing with network 999. As can be appreciated, the network 999 can be a public network, such as the Internet, or a private network such as an LAN or WAN network, or any combination thereof and can also include PSTN or ISDN sub-networks. The network 999 can also be wired, such as an Ethernet network, or can be wireless such as a cellular network including EDGE, 3G and 4G wireless cellular systems. The wireless network can also be WiFi, Bluetooth, or any other wireless form of communication that is known.

The controller 205 further includes a display controller 408, such as a NVIDIA GeForce GTX or Quadro graphics adaptor from NVIDIA Corporation of America for interfacing with display 410, such as a Hewlett Packard HPL2445w LCD monitor. A general purpose I/O interface 412 interfaces with a keyboard and/or mouse 414 as well as a touch screen panel 416 on or separate from display 410. General purpose I/O interface 412 also connects to a variety of peripherals 418 including printers and scanners, such as an OfficeJet or DeskJet from Hewlett Packard.

A sound controller 420 is also provided in the controller 205, such as Sound Blaster X-Fi Titanium from Creative, to interface with speakers/microphone 422 thereby providing sounds and/or music. The speakers/microphone 422 can also be used to accept dictated words as commands for controlling the controller 205 or for providing location and/or property information with respect to the target property.

The general purpose storage controller 424 connects the storage medium disk 404 with communication bus 426, which may be an ISA, EISA, VESA, PCI, or similar, for interconnecting all of the components of the controller 205. A description of the general features and functionality of the display 410, keyboard and/or mouse 414, as well as the display controller 408, storage controller 424, network controller 406, sound controller 420, and general purpose I/O interface 412 is omitted herein for brevity as these features are known.

A face camera controller 440 is provided in the controller 205 to interface with the face camera 201.

An environment camera controller 442 is provided in the controller 205 to interface with the environment camera 203.

A warning/guidance device controller 444 is provided in the controller 205 to interface with the warning/guidance device 209. Alternatively, display 410, speaker 422, and/or peripherals 418 may be used in place of or in addition to the warning/guidance device 209 to provide warning and/or guidance.

A relevance and priority database controller 446 is provided in the controller 205 to interface with the relevance and priority database 207. Alternatively, the relevance and priority database 207 may be included in disk 404 of the controller 205.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions may be executed out of order from that shown or discussed, including substantially concurrently or in reverse order, depending upon the functionality involved, as would be understood by those skilled in the art.

While certain embodiments have been described, these embodiments have been presented by way of example only, and are not intended to limit the scope of the inventions. Indeed, the novel methods, apparatuses and systems described herein may be embodied in a variety of other forms; furthermore, various omissions, substitutions and changes in the form of the methods, apparatuses and systems described herein may be made without departing from the spirit of the inventions. The accompanying claims and their equivalents are intended to cover such forms or modifications as would fall within the scope and spirit of the inventions.

The invention claimed is:

1. A method comprising:
   determining a probability of attention of an operator of a vehicle to one or more areas of interest in an environment of a vehicle based on relevance and priority values corresponding to the one or more areas of interest;
   determining an attention deficiency based on the determined probability of attention and eye movements of the operator of the vehicle; and
   providing information to a warning or guidance device based on the determined attention deficiency.

2. The method of claim 1, wherein the one or more areas of interest includes at least one of a pedestrian, a cyclist, a traffic light, a traffic sign, an animal, an object, or another vehicle.

3. The method of claim 1, wherein the step of determining the probability of attention includes:
   determining linear distances of the one or more areas of interest from the vehicle;
   determining saliencies of the one or more areas of interest;
   detecting event frequencies within the one or more areas of interest; and
   determining the probability of attention of the operator of the vehicle to the one or more areas of interest based on the linear distances, the saliencies, the event frequencies, and the relevance and priority values.

4. The method of claim 3, wherein the step of determining the linear distances includes:
   setting a linear distance of an area of interest to zero when an angle between a line of sight of the operator of the vehicle and a line of sight corresponding to the area of interest is greater than or equal to 90 degrees; and
   setting the linear distance of the area of interest to a distance between the area of interest and the vehicle divided by a cosine of the angle between the line of sight of the operator of the vehicle and the line of sight corresponding to the area of interest when said angle is smaller than 90 degrees.

5. The method of claim 1, wherein the step of determining the attention deficiency includes:
   detecting facial features of the operator of the vehicle by feature point extraction algorithms based on face images, the facial features including one or more of eye corners, upper eyelids, or lower eyelids;
   determining an iris location based on the detected facial features;
   determining gaze pointers based on the iris location and images of the environment of the vehicle;
   determining gaze fixation dwell times based on the gaze pointers;
   determining an observed attention level based on gaze fixation dwell times; and
   determining the attention deficiency based on the observed attention level and the probability of attention.

6. The method of claim 1, wherein the step of providing the information includes:
   providing, based on the determined attention deficiency, one or more of a failed-to-look warning, a look-but-fail-to-see warning, an audio/visual warning, and guidance information.

7. The method of claim 1, further comprising determining the one or more areas of interest in the environment of the vehicle based on environmental images of the environment of the vehicle.

8. The method of claim 1, further comprising obtaining the relevance and priority values from a relevance and priority database.

9. The method of claim 1, wherein the eye movements are detected based on face images of the operator.

10. An apparatus comprising:
    a warning or guidance device; and
    controller circuitry configured to
      determine a probability of attention of an operator of the vehicle to one or more areas of interest in an environment of a vehicle based on relevance and priority values corresponding to the one or more areas of interest;
      determine an attention deficiency based on the determined probability of attention and eye movements of the operator of the vehicle; and provide information to the warning or guidance device based on the determined attention deficiency.

11. The apparatus of claim 10, wherein the one or more areas of interest includes at least one of a pedestrian, a cyclist, a traffic light, a traffic sign, an animal, an object, or another vehicle.

12. The apparatus of claim 10, wherein the controller circuitry is further configured to:
determine linear distances of the one or more areas of interest from the vehicle;
determine saliencies of the one or more areas of interest;
detect event frequencies within the one or more areas of interest; and
determine the probability of attention of the operator of the vehicle to the one or more areas of interest based on the linear distances, the saliencies, the event frequencies, and the relevance and priority values.

13. The apparatus of claim 12, wherein the controller circuitry is further configured to:
set a linear distance of an area of interest to zero when an angle between a line of sight of the operator of the vehicle and a line of sight corresponding to the area of interest is greater than or equal to 90 degrees; and
set the linear distance of the area of interest to a distance between the area of interest and the vehicle divided by a cosine of the angle between the line of sight of the operator of the vehicle and the line of sight corresponding to the area of interest when said angle is smaller than 90 degrees.

14. The apparatus of claim 10, wherein the controller circuitry is further configure to:
detect facial features of the operator of the vehicle by feature point extraction algorithms based on face images, the facial features including one or more of eye corners, upper eyelids, or lower eyelids;
determine an iris location based on the detected facial features;
determine gaze pointers based on the iris location and images of the environment of the vehicle;
determine gaze fixation dwell times based on the gaze pointers;
determine an observed attention level based on gaze fixation dwell times; and
determine the attention deficiency based on the observed attention level and the probability of attention.

15. The apparatus of claim 10, wherein the controller circuitry is further configured to provide, based on the determined attention deficiency, one or more of a failed-to-look warning, a look-but-fail-to-see warning, an audio/visual warning, and guidance information to the warning or guidance device.

16. The apparatus of claim 10, wherein the controller circuitry is further configured to determine the one or more areas of interest in the environment of the vehicle based on environmental images of the environment of the vehicle.

17. The apparatus of claim 10, further comprising a relevance and priority database that stores a plurality of relevance and priority values corresponding to a plurality of areas of interest.

18. The apparatus of claim 17, wherein the controller circuitry is further configured to obtain the relevance and priority values from the relevance and priority database.

19. The apparatus of claim 10, wherein the controller circuitry is further configured to detect the eye movements based on face images of the operator.

20. A non-transitory computer-readable medium storing a program that, when executed by a processor, causes the processor to perform a method, the method comprising:
determining a probability of attention of an operator of a vehicle to one or more areas of interest in an environment of a vehicle based on relevance and priority values corresponding to the one or more areas of interest;
determining an attention deficiency based on the determined probability of attention and eye movements of the operator of the vehicle; and
providing information to a warning or guidance device based on the determined attention deficiency.

* * * * *